United States Patent
Dupuis et al.

(10) Patent No.: US 6,537,583 B1
(45) Date of Patent: Mar. 25, 2003

(54) METHOD FOR PREPARING CAPSULES CONSISTING OF A LIQUID ACTIVE MATERIAL CORE ENCLOSED IN A MINERAL COATING

(75) Inventors: Dominique Dupuis, Crepy-en-Valois (FR); Catherine Jourdat, Sainte-Foy-les-Lyon (FR)

(73) Assignee: Rhodia Chimie, Boulogne Billancourt Cedex (FR)

( * ) Notice: Subject to any disclaimer, the term of this patent is extended or adjusted under 35 U.S.C. 154(b) by 0 days.

(21) Appl. No.: 09/830,797

(22) PCT Filed: Oct. 27, 1999

(86) PCT No.: PCT/FR99/02615

§ 371 (c)(1),
(2), (4) Date: Jul. 19, 2001

(87) PCT Pub. No.: WO00/25908

PCT Pub. Date: May 11, 2000

(30) Foreign Application Priority Data

Oct. 30, 1998 (FR) .............................................. 98 13692

(51) Int. Cl.[7] .............................. A61K 9/16; B01J 13/02
(52) U.S. Cl. ........................ 424/490; 264/4.1; 264/4.3; 264/4.6; 264/4.7; 264/5; 428/402.2; 424/489; 424/491; 424/455
(58) Field of Search .......................... 264/4.1, 4.3, 4.6, 264/4.7, 5; 428/402.2; 424/489, 490, 491, 455

(56) References Cited

U.S. PATENT DOCUMENTS

| 3,954,666 A | * | 5/1976 | Marquisse et al. | .......... 428/402 |
| 3,954,678 A | * | 5/1976 | Marquisse | ............... 210/198.2 |

FOREIGN PATENT DOCUMENTS

| EP | 0 465 235 | 1/1992 |
| FR | 0 401 619 | 3/1979 |

* cited by examiner

*Primary Examiner*—Samuel A. Acquah

(57) ABSTRACT

The invention concerns a method for preparing mineral capsules consisting of aqueous liquid core enclosed in mineral coating, said method consisting in: 1) emulsifying an aqueous fluid in a phase non-miscible with said aqueous fluid so as to disperse it therein in the form of droplets; 2) contacting, in the resulting emulsion, at least a zirconium, silicon, aluminium and/or a transition metal capable of being hydrolysed or subjected to condensation polymerisation in temperature and pH conditions suitable for forming a precipitate consisting of the corresponding oxide or hydroxide; 3) recuperating the resulting mineral capsules and, if required, purifying them. Said method is characterised in that the formation of the mineral precipitate in the second step is carried out in the presence of an amphiphilic surfactant system present in the emulsion and capable of concentrating the deposit of mineral particles of said precipitate formed in the interface of the aqueous droplets and the hydrophobic phase and of effectively blocking their diffusion inside the droplets.

28 Claims, 1 Drawing Sheet

METHOD FOR PREPARING CAPSULES CONSISTING OF A LIQUID ACTIVE MATERIAL CORE ENCLOSED IN A MINERAL COATING

This application is an application under 35 U.S.C. Section 371 of International Application Number PCT/FR99/02615 filed on Oct. 27, 1999.

A subject matter of the present invention is a process of use in the preparation of capsules comprising inorganic shells of controlled thickness and having a core composed of an aqueous fluid in which at least one active material can be dispersed and/or dissolved.

Various microencapsulation techniques are already available for packaging varied active materials. This type of packaging is favored in particular when it is desired to mask the taste of an active material, to control its release over time and/or to protect it from its surrounding medium.

Overall, two types of encapsulation techniques can be distinguished.

The first type results in a "reservoir" system. The active material is immobilized at the center of a capsule by a membrane of polymeric nature. Capsules of this type are generally obtained by the technique referred to as the interfacial polycondensation technique. It consists in bringing about the condensation of a polymer at the interface of two immiscible liquids. Microspheres with a mean diameter of 10 to 30 $\mu$m composed of a liquid core surrounded by a thin polymer envelope representing only 5 to 15% of the total weight of the capsule are thus obtained. The polymer membrane provides for protection with respect to the external medium of the liquid core, which generally comprises an active material, and its porosity makes it possible to control the diffusion thereof out of the capsule. This type of encapsulation is provided in particular for the packaging of active materials of pesticidal type for which it is desired to control the release over time. Techniques referred to as coating by spraying, coating by phase separation and coating by solidification also result in this "reservoir" system.

The second type of encapsulation technique results in a "matrix" system. The active material being encapsulated is dispersed within either an organic network of polymer type or an inorganic network, such as, for example, silica. Mention may more particularly be made, by way of representation of this type of encapsulation, of the technique of inorganic encapsulation by the sol-gel route. The convention sol-gel technique consists in initiating the hydrolysis and the polycondensation of a metal alkoxide in an aqueous or aqueous/alcoholic medium comprising the active material to be packaged. This results in the formation of a gel in which said active material is found dispersed, which gel leads, after drying, to a porous glass. According to an alternative form of the sol-gel technique, referred to as the emulsion sol-gel technique, a network of inorganic oxide, generally of silica, is formed from a molecular precursor of the alkoxide type in the presence of a water-in-oil emulsion in which the active material is dispersed. The active material present during the stage of hydrolysis and the condensation of the inorganic material is then trapped in the powder.

The present invention is targeted more specifically at providing a novel encapsulation technique which makes it possible to produce capsules comprising a core composed of an aqueous fluid surrounded by an inorganic shell.

More specifically, a subject matter of the present invention is a process for preparing inorganic capsules composed of an aqueous liquid core surrounded by an inorganic shell, said process comprising:

1) emulsifying an aqueous fluid within an organosoluble phase which is immiscible with said aqueous fluid, so as to disperse it therein in the form of droplets,
2) bringing into contact, within the emulsion thus obtained, at least one hydrolyzable and polycondensable compound of zirconium, of silicon, of aluminum and/or of a transition metal under temperature and pH conditions favorable to the formation of an inorganic precipitate composed of the corresponding oxide or hydroxide, and
3) recovering the inorganic capsules thus formed and, if appropriate, purifying them, said process being characterized in that the formation of the inorganic precipitate in stage 2 is carried out in the presence of an amphiphilic surfactant system present in the emulsion and capable of concentrating the deposition of the inorganic particles of the precipitate formed at the interface of the aqueous droplets and of the organosoluble phase and of effectively blocking the diffusion of these inorganic particles within said droplets.

In the context of the present invention, it is possible to envisage packaging simply an aqueous fluid, such as water. According to this alternative form, the water is used directly as active material. It can thus represent an agent for delayed hydrolysis of chemical compounds, such as functionalized silicones.

BRIEF DESCRIPTION OF THE DRAWINGS

In the attached drawings.

Figure 1:
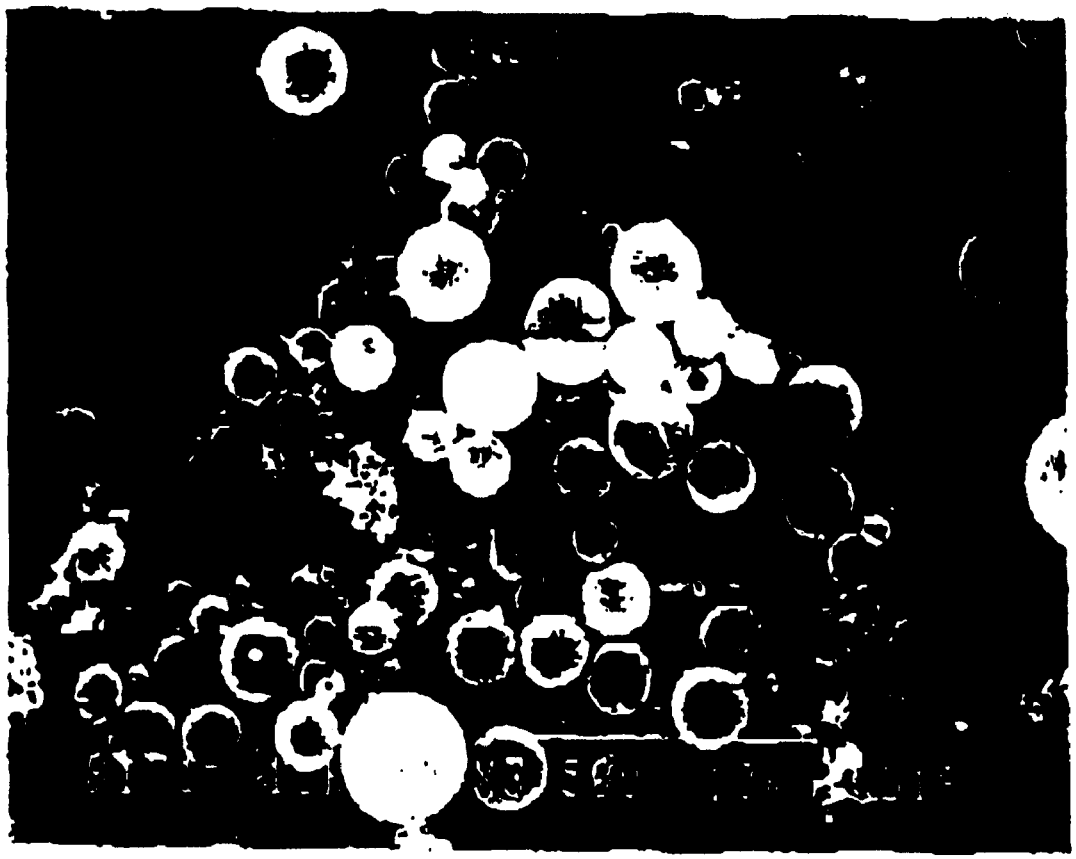
FIG. 1 represents a scanning microscopy photograph of capsules of silica shell.

According to a second favored alternative form of the invention, the aqueous medium constituting the core of the capsules which are obtained according to the invention comprises at least one active material.

The claimed process thus proves to be of very particular use for the formulation, in solid form, of products conventionally used in liquid formulations or for the packaging of active materials which have to be stored in a liquid environment. This is in particular the case with biological active materials, such as cells, microorganisms or enzymes. The claimed process advantageously makes possible, in future, the packaging of active materials of this type in their natural biological media and under mild experimental conditions, in particular in terms of temperatures. This is because the active material being encapsulated is not exposed to temperature and, if appropriate, pH values capable of harming it.

The active materials capable of being encapsulated according to the claimed process can be compounds of industrial interest in the fields of fermentation, plant protection, cosmetics, pharmaceuticals and/or the chemical industry.

It is thus possible to envisage encapsulating, according to the claimed process, water-soluble catalysts, such as rare earth metal triflates, borates, reactive latices which it is desired to release in a matrix of concrete type, for example, or compounds of cosmetic interest, such as essential oils. Likewise, they can be synthetic active materials, such as chemical compounds, for instance pharmaceutical or plant-protection active principles, for instance bactericides, fungicides and pesticides, for example. Finally, within the meaning of the invention, the term "active material" includes active materials referred to as biological active materials, such as cells of bacteria type, microorganisms, proteins and antibodies, for example.

These active materials, depending on their water-soluble nature, are either dissolved or dispersed in the aqueous liquid medium.

The inorganic shell obtained according to the process of the invention has the two-fold advantage of efficiently protecting the liquid medium and the active material(s) which it comprises and, if appropriate, of allowing it to be exchanged with the medium surrounding the capsules. This is achieved in particular by adjusting the degree of porosity of the inorganic capsules obtained according to the invention.

According to a first alternative form of the invention, the inorganic capsules obtained can be non-porous. This specific property is more particularly advantageous when it is desired essentially to provide effective protection of an aqueous medium, incorporating or not incorporating an active material, with respect to its surrounding medium. In contrast to the microcapsules obtained by interfacial polycondensation, which are composed of an organic shell, the capsules obtained according to the invention are much stronger mechanically, thermally and chemically because of the inorganic nature of their shell. In this specific case, the aqueous medium and, if appropriate, the active material which it comprises are generally released by splitting the capsule or by induced decomposition of the latter.

According to a second alternative form of the invention, the capsules obtained can be porous and this porosity is controllable. This is of significant advantage when it is desired, in addition to protecting the aqueous medium constituting the core of the capsules, to allow it to be exchanged with the medium surrounding said capsules.

In fact, this adjustment of the porosity and that of the size of the capsules are accomplished mainly through the choice of the inorganic material constituting the inorganic shell or more specifically the choice of the precursor of this material. This aspect of the invention is discussed in more detail below.

The problem more particularly posed and solved according to the present invention relates to the preservation of a significant volume of an aqueous liquid medium at the center of the inorganic capsules generated.

Generally, the emulsion hydrolysis and polycondensation of precursors of silicon alkoxide type, for example, generate inorganic particles which naturally diffuse to the center of the droplets of the aqueous fluid, thus resulting in the formation of inorganic matrices within which the active material optionally present in the aqueous medium is trapped by the inorganic powder formed and is thus encountered dispersed in a homogeneous manner. This is the emulsion sol-gel technique mentioned above.

Surprisingly, the inventors have demonstrated that it is possible to control this phenomenon of natural diffusion by carrying out the hydrolysis and the polycondensation of the hydrolyzable and polycondensable inorganic precursor or precursors in the presence of a surfactant system of amphiphilic nature.

Within the meaning of the invention, the term "amphiphilic surfactant system" is understood to denote either a single surfactant, in which case it is a compound within which two regions coexist possessing very different solubilities which are sufficiently far from one another to behave independently, or a combination of at least two compounds possessing very different solubilities, one having, for example, a hydrophilic behavior and the other a hydrophobic behavior. Generally, these two regions or compounds respectively comprise at least one hydrophilic group and one or more long chains of hydrophobic nature.

Consequently, the surfactant system employed according to the invention can be represented by a single compound which will then be introduced prior to carrying out the second stage, that is to say the hydrolysis and polycondensation stage, or can result from an in situ interaction of at least two surfactants, such as, for example, an organosoluble surfactant initially present in the organosoluble phase and a water-soluble compound present in the aqueous fluid. It is also possible to envisage a coupling between a first organosoluble agent and a second organosoluble agent of ionic nature, such as a quaternary ammonium. The two compounds meet at the interface of the droplets formed during the emulsification. By their interaction, they contribute, first, to stabilizing the system by decreasing the interfacial tension at the interface of the droplets and probably act as a steric or electrostatic barrier with respect to particles of the inorganic material which precipitates.

In the case of a water-soluble/lipophilic coupling, it is probable that strong attractions of hydrogen bond type displayed in the surfactant system generate a viscosity gradient from the center of the droplets to the interface and produce significant steric hindrance at the interface of the aqueous droplets, thus creating an effective diffusion barrier at the interface of the droplets and of the organo-soluble phase.

It is also possible to envisage the appearance of an interaction, for example of complexing type, between the surfactant or surfactants and the material constituting the inorganic shell.

In addition to this role of barrier to the diffusion of the inorganic particles within the aqueous droplets, the surfactant system selected according to the invention also preferably contributes to the stabilization of the emulsion. More specifically, it opposes the coagulation of the aqueous droplets and consequently the destabilization of the emulsion. Likewise, it contributes to the colloidal stability during the generation of the inorganic shell.

In so far as the aim, in the context of the present invention, is to stabilize an inverse emulsion, the surfactant system will preferably be chosen so as either to comprise at least one surfactant possessing an HLB value preferably of less than 7 or to have, in its structure, at least one branch or group having this HLB value.

The term "HLB" denotes the ratio of the hydrophilicity of the polar groups of the surfactant molecules to the hydrophobicity of the lipophilic part of these same molecules.

Of course, it is also possible to envisage incorporating one or more additional anionic or cationic surfactants in the emulsion, which surfactants are intended essentially to provide for the stabilization of the emulsion. In this specific embodiment, this or these surfactant(s) will be separate from the amphiphilic surfactant defined above and will be chosen so as not to interfere with the process for the preparation of the capsules.

The embodiment employing at least two separate compounds capable of interacting to result in a surfactant system capable of effectively opposing the diffusion of the inorganic particles into the aqueous droplets and of stabilizing said emulsion is more particularly preferred in the claimed process. In this specific case, the two compounds are preferably respectively present in the aqueous fluid and the organosoluble phase and interact with one another during the emulsification of the aqueous fluid in the organosoluble phase.

This option has the advantage of conferring, on the corresponding emulsion, a satisfactory stability from its formation. Furthermore, it proves possible, if necessary, by appropriately selecting the agents constituting the amphiphilic surfactant system, to adjust the pH to a value compatible with the active material.

As regards the emulsification, it can be carried out by applying mechanical energy and/or ultrasound. The size of the droplets obtained on conclusion of the emulsification stage can be between approximately 0.1 and 10 µm.

The compound, present in the aqueous fluid as surfactant and not as solvent, preferably has a viscosifying effect.

More particularly, this compound can be a compound chosen from sugars and their derivatives. Oses (or monosaccharides), osides and highly depolymerized polyholosides are suitable in particular. These are understood to mean compounds for which the weight-average molar mass is more particularly less than 20 000 g/mol.

Mention may in particular be made of linear or cyclic $C_3$ to $C_6$ and preferably $C_5$ or $C_6$ mono-saccharides, such as fructose, mannose, galactose, talose, gulose, allose, altrose, idose, arabinose, xylose, lyxose and ribose.

Osides are compounds which result from the condensation, with elimination of water, of ose molecules with non-glucide molecules. Among osides, holosides, which are formed by the combination of exclusively glucide units, and more particularly oligoholosides (or oligosaccharides), which comprise only a restricted number of these units, that is to say a number generally of less than or equal to 10, are preferred. Mention may be made, as examples of oligoholosides, of oligosaccharols, sucrose, lactose, cellobiose or maltose.

Suitable highly depolymerized polyholosides (or polysaccharides) are described, for example, in the work by P. Arnaud entitled "Cours de chimie organique" [Course in Organic Chemistry], published by Guthier-Villars, 1987. More particularly, polyholosides for which the weight-average molecular mass is more particularly less than 20 000 g/mol are employed.

Mention may be made, as nonlimiting examples of highly depolymerized polyholosides, of polysaccharides, such as dextran, starch, xanthan gum, carrageenans and galactomannans, such as guar gum or locust bean gum. These polysaccharides preferably exhibit a melting weight of greater than 100° C. and a solubility in water of between 10 and 500 g/l.

Gum arabic, gelatin and their fatty derivatives, such as fatty acid sucroesters, carbohydrate alcohols of sorbitol or mannitol type, carbohydrate ethers, such as cellulose derivatives, for instance methyl, ethyl, carboxymethyl, hydroxyethyl and hydroxypropyl ethers of cellulose, and glycerols, pentaerythrol, propylene glycol, ethylene glycol, nonviscous diols and/or poly(vinyl alcohol)s are also suitable for the invention.

It is preferably a hydrocolloid. Mention may in particular be made, as representatives of compounds of this type, of alginates, polysaccharides of natural gum type, such as carrageenans, xanthan gum and guar gum, and very particularly cellulose derivatives.

It is preferably a cellulose derivative and more preferably hydroxyethylcellulose.

The organosoluble surfactant(s) present in the hydrophobic phase can be chosen from fatty alcohols, triglycerides, fatty acids, sorbitan esters or fatty amines, these compounds being or not being in a polyalkoxylated form, fat-soluble lecithins, poly-alkylene dipolyhydroxystearates, quaternary ammonium salts, monoglycerides, polyglycerol esters, polyglycerol polyricinoleate and lactic esters.

The fatty alcohols generally comprise from 6 to 22 carbon atoms. The triglycerides can be triglycerides of plant or animal origin (such as lard, tallow, groundnut oil, butter oil, cottonseed oil, linseed oil, olive oil, fish oil, copra oil or coconut oil).

The fatty acids are fatty acid esters (such as, for example, oleic acid or stearic acid).

The sorbitan esters are fatty acid cyclized sorbitol esters, the fatty acid comprising from 10 to 20 carbon atoms, such as lauric acid, stearic acid or oleic acid.

According to a preferred form of the invention, this surfactant is a sorbitan ester as defined above and more preferably sorbitan sesquioleate.

As emerges from the preceding account, the compound present in the aqueous fluid has to interact with the organosoluble surfactant present in the hydrophobic phase to result in a surfactant system capable of constituting an effective diffusion barrier with respect to the particles of the inorganic precipitate. Consequently, their respective choices have to be made while taking into account this requirement.

Of course, the nature of the active material to be encapsulated and the composition of the inorganic shell of the capsules which are prepared according to the invention are also determining factors in the choice of the surfactant system and the assessment of the respective amounts of the two corresponding compounds. These adjustments in fact come within the competence of the person skilled in the art.

In the specific case where the use of a single compound of amphiphilic type is favored according to the invention, those corresponding to the general formula I:

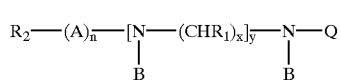

in which:

R$_2$ represents an alkyl or alkenyl radical comprising 7 to 22 carbon atoms, R$_1$ represents a hydrogen atom or an alkyl radical comprising 1 to 6 carbon atoms, A represents a (CO) or (OCH$_2$CH$_2$) group, n has the value 0 or 1, x has the value 2 or 3, y has the value 0 to 4, Q represents an —R$_3$—COOM radical with R$_3$ representing an alkyl radical comprising 1 to 6 carbon atoms and M represents a hydrogen atom, an alkali metal, an alkaline earth metal or a quaternary ammonium group in which the radicals bonded to the nitrogen atom, which are identical or different, are chosen from hydrogen or an alkyl or hydroalkyl radical possessing 1 to 6 carbon atoms, and B represents H or Q, are very particularly suitable.

Preferably, M represents a hydrogen atom, sodium, potassium and an NH$_4$ group.

Use is more particularly made, among these surfactants corresponding to the formula I, of amphoteric derivatives of alkylpolyamines, such as Amphionic XL®, Mirataine H2C-HA®, sold by Rhodia Chimie, and Ampholac 7T/X®, sold by Berol Nobel.

Use may also be made of a main nonionic surfactant, the hydrophilic part of which comprises one or more saccharide units(s). Said saccharide units generally comprise from 5 to 6 carbon atoms. These can derive from sugars, such as fructose, glucose, mannose, galactose, talose, gulose, allose, altose, idose, arabinose, xylose, lyxose and/or ribose.

Mention may be made, among these surfactants of saccharide structure, of alkylpolyglycosides. The latter can be obtained by condensation (for example by acid catalysis) of glucose with primary fatty alcohols (U.S. Pat. Nos. 3,598, 856; 4,565,647; EP-A-132 043; EP-A-132 046; Tenside Surf. Det., 28, 419, 1991, 3; Langmuir, 1993, 9, 3375–3384) exhibiting a $C_4$–$C_{20}$ alkyl group, preferably of the order of 1.1 to 1.8 per mole of alkylpolyglycoside (APG); mention may in particular be made of those sold respectively under the names Glucopon 600 EC®, Glucopon 650 EC® and Glucopon 225 CSUP®, by Henkel.

By way of illustration, the concentration of amphiphilic surfactant system can be between approximately 1% and 10% by weight with respect to the organosoluble phase.

As regards the composition of the inorganic shell, it is composed of at least one oxide and/or hydroxide of aluminum, of silicon, of zirconium and/or of a transition metal.

The term "transition metal" is understood to mean more particularly the metals from the fourth period ranging from scandium to zinc, in so far, of course, as the latter are compatible in terms of harmlessness with the targeted application. It relates more particularly to an oxide and/or hydroxide of titanium, manganese, iron, cobalt, nickel or copper. It should be noted that this inorganic shell can comprise oxides and/or hydroxides of different natures. Oxides and/or hydroxides of silicon, aluminum, titanium and zirconium are particularly well suited to the invention.

According to a preferred embodiment of the invention, the inorganic shell derives from the hydrolysis and the polycondensation of one or more alkoxides of formula II:

$$M(R)_n(P)_m \qquad \text{II}$$

in which:
M represents an element chosen from titanium, manganese, iron, cobalt, nickel, silicon, aluminum or zirconium,
R is a hydrolyzable substituent,
n is an integer between 1 and 6,
P is a nonhydrolyzable substituent, and
m is an integer between 0 and 6.
According to a preferred form of the invention:
M is chosen from silica, aluminum, titanium and zirconium,
R is a group chosen from $C_1$ to $C_{18}$ and preferably $C_2$ to $C_9$ alkoxy groups and/or from aryloxy groups and n is an integer between 2 and 4, and
P is a group chosen from alkyls, aryls or alkenyls comprising from 1 to 18 carbon atoms and preferably $C_8$ to $C_{12}$ alkyls, aryls or alkenyls.

As regards R, it is preferably a $C_1$ to $C_6$ and more preferably $C_2$ to $C_4$ alkoxy group. This alkoxy can, if appropriate, be substituted by a $C_1$ to $C_4$ alkyl or alkoxy group or a halogen atom. In the general formula II, R can, of course, represent identical or different alkoxy groups.

Of course, several compounds of formula II can be employed in the claimed process.

As indicated above, it proves to be possible, through the choice of this hydrolyzable and polycondensable inorganic compound, to adjust the porosity and the size of the capsules.

The porosity of the inorganic shell makes it possible to effectively protect the encapsulated active material from any damage capable of being caused to it by the external medium while allowing it, if appropriate, to interact with the medium.

As regards the size of the capsules, the fact of being able to control it also makes it possible to adjust it according to the constraints related in particular to the size of aqueous volume constituting the nucleus of the capsules, the encapsulated active material and the amount of these active materials.

Likewise, a more or less hydrophobic nature can be conferred on the capsule by varying the nature and, for example, the length of the alkyl and/or alkoxy chains constituting this hydrolyzable and polycondensable inorganic compound.

Generally, the hydrolysis and the polycondensation of this inorganic precursor are achieved either spontaneously, by bringing together the inorganic precursor and the emulsion, or are initiated by adjustment of the pH and/or of the temperature of the emulsion to a value favorable to their expression. This adjustment can relate in particular to the presence in the emulsion of water-soluble ions, such as $NH_4OH$, $NaOH$ or $HCl$, or organosoluble ions of amine type. These adjustments come within the competence of a person skilled in the art.

According to a preferred alternative form of the present invention, the inorganic shell obtained according to the invention is based on silicon oxide. It derives from the precipitation of at least one silicate.

Mention may more particularly be made, as silicates suitable for the present invention, of alkylorthosilanes, alkoxyorthosilane and haloalkyl-silanes, and more preferably of tetramethyl orthosilicate, TMOS, tetraethyl orthosilicate, TEOS, or tetrapropyl orthosilicate, TPOS.

According to a specific embodiment of the invention, the inorganic capsule is obtained by interfacial hydrolysis and polycondensation at ambient temperature of a silicon alkoxide in the presence of an agent for hydrolyzing and condensing said silicon alkoxide.

The hydrolysis of these silicon alkoxides can equally well be carried out by acid catalysis as by basic catalysis, with the proviso that the corresponding oxides and/or hydroxides are obtained in a pulverulent form.

According to a specific form of the invention, a silicon alkoxide, such as tetraethyl orthosilicate, TEOS, is employed in the presence of aqueous ammonia as hydrolysis and polycondensation agent.

The organic phase is generally a water-immiscible oily phase and is preferably composed of an oil chosen from vegetable, animal and mineral oils. It can, for example, be a liquid paraffin or a silicone oil.

However, it is also possible to envisage employing other organic solvents, such as perfluorinated solvents, with the proviso that these solvents are used under appropriate conditions, for example in the form of a mixture, to result in an emulsion with the aqueous solvent.

Mention may in particular be made, as organo-soluble phase which is very particularly suitable for the invention, of the solvent Isopar®, which is an isoparaffin sold by Exxon Chemicals.

This organosoluble phase comprises at least one organosoluble surfactant, which is preferably chosen from sorbitan esters and more preferably is represented by sorbitan sesquioleate.

As regards the aqueous phase, it comprises at least one hydrocolloid and optionally the agent for hydrolyzing and polycondensing the hydrolyzable and polycondensable inorganic precursor. The hydrocolloid is present therein in an amount suitable for providing it with a surfactant role.

As regards the hydrocolloid, it is preferably a cellulose derivative and more preferably hydroxy-ethylcellulose.

Of course, the pH of the aqueous phase is adjusted according to the requirements related to the production of the capsules and, if appropriate, to preserving the integrity of the active material to be encapsulated.

This pH is generally between 8 and 11, it being possible, however, for the reaction to be carried out in an acidic medium.

Generally, the size of the capsules obtained according to the invention is between 1 and about ten micrometers and preferably 30 µm. The size of the particles of the inorganic material constituting the shell of these capsules varies, for its part, between a few nanometers and 200 nanometers.

As regards more particularly the thickness of the inorganic shell, it can vary between a few nanometers and 200 nanometers.

These capsules can also be characterized by the amount of aqueous fluid which the inorganic shell retains by introducing the retention of the capsule parameter. This parameter corresponds to the ratio of the mass of the inorganic shell to the mass of the aqueous medium constituting the core of the capsule.

By way of illustration, in the specific case of capsules with a silica shell, this retention parameter can vary between 3 to 20% of silica/aqueous medium.

When the shell is too porous, the retention of the capsule is low; these parameters are thus varied by fixing the size of the particles of the material which is generated at the interface in order to alter the retention of the capsules.

It is also possible to envisage modifying the porosity of the inorganic shell of capsules obtained according to the invention via an additional treatment which consists, for example in coating them with a surface composition intended to temporarily or definitively close off their pores. This can be of advantage in particular when it is desired to control, in location or all the time, the exchanges between the liquid core of the capsule and its surrounding medium. Thus it is that a pH-sensitive surface coating will only be able to disintegrate for a predetermined pH value and thus will make possible the exchanges between the liquid core and the active material which it comprises and its external medium only from this value.

The examples and figures which follow are presented by way of illustration and without implied limitation of the subject matter of the present invention.

FIG. 1

Scanning microscopy photograph of capsules with a silica shell comprising Rhodamine.

EXAMPLE 1

Production of Capsules with a Silica Shell Incorporating an Aqueous Phase Comprising Rhodamine Overall Composition of the Reaction Medium

| aqueous phase: | $H_2O$ | 43.40 g |
| --- | --- | --- |
| | Rhodamine | 0.430 g |
| | | (1% with respect to the water) |
| | Hydroxyethylcellulose | 2.61 g |
| | 20% $NH_3$ | 0.5 g |
| organic phase: | Sorbitan sesquioleate (Arlacel 83 ® ((ICI)) | 17.35 g |
| | Isopar M ® solvent, sold by Exxon Chemical | 850 g |
| | Tetramethyl orthosilicate | 28.5 g |

Preparation of the Aqueous Phase

The rhodamine is homogenized on a water bath at 40° C. for 20 minutes. The hydroxyethylcellulose and then the aqueous ammonium solution are added thereto.

Preparation of the Organic Phase

The sorbitan sesquioleate is dissolved in the Isopar M®.

Preparation of the Emulsion

The organic phase is stirred using an Ultraturrax at the minimum power, that is to say at approximately 3 500 rpm. The aqueous phase is added thereto while continuing to stir. The stirring power is subsequently increased to 6 000 rpm for 5 minutes. An orange-red emulsion is obtained.

Synthesis of the Capsules

The emulsion prepared previously is introduced into a three-necked flask equipped with a magnetic bar. The tetrameth orthosilicate, TMOS, (28.5 g) is added thereto at ambient temperature over approximately 1 hour with a flow rate of the order of 0.5 ml/min. The particles obtained are separated and washed once with methanol and then in purified water by centrifuging at 1 000 PR for 30 minutes, and then dried at ambient temperature overnight.

Characterizations

The particles obtained have a size of 5 to 20 microns (scanning microscopy). They are spherical in shape (FIG. 1).

EXAMPLE 2

Production of Silica Capsules Incorporating an Antibacterial

Overall Composition of the Reaction Medium

| Aqueous phase: | Water | 10.9 g |
| --- | --- | --- |
| | Hydroxyethylcellulose | 0.65 g |
| | 20% $NH_3$ | 0.926 g |
| | Nipagin M ® (anti-bacterial sold by Sipca) | 0.109 g |
| Organic phase: | Arlacel 83 ® | 4.34 g |
| | Isopar M ® | 212.5 g |
| | Methyl silicate | 7.12 g* |

*introduced continuously.

Preparation of the Aqueous Phase

The HEC solution is homogenized on a water bath at 40° C. for 20 minutes, then the Nipagin is added and finally the aqueous ammonia is added.

Preparation of the Organic Phase

The sorbitan sesquioleate is dissolved in the Isopar M.

Preparation of the Emulsion

The organic phase is added using an Ultraturrax with a power of 6 000 r/min and then the aqueous phase is added. After addition of the aqueous solution, stirring is maintained for 5 minutes.

Synthesis of the Capsules

The emulsion prepared previously is introduced into a three-necked flask equipped with a magnetic bar. The tetramethyl orthosilicate (7.12 g) is added thereto at ambient temperature with a flow rate of 0.12 ml/min. The particles thus obtained are separated and washed once with hexane and then dried at 30° C.

Spherical silica particles of 5 to 10 microns (observed by scanning microscopy) are obtained. The membrane structure of the capsule is demonstrated by transmission electron microscopy. The size of the particles which constitute the shell is of the order of 50 mm.

What is claimed is:

1. A process for the preparation of inorganic capsules composed of an aqueous liquid core surrounded by an inorganic shell, said process comprising the steps of:

1) emulsifying an aqueous fluid within an organosoluble phase which is immiscible with said aqueous fluid, so as to disperse it therein in the form of aqueous droplets, 2) bringing into contact, within the emulsion thus obtained, at least one hydrolyzable and polycondensable compound of zirconium, silicon, aluminum or a transition metal under temperature and pH conditions for forming an inorganic precipitate composed of an oxide or hydroxide of the compound, and 3) recovering and optionally purifying inorganic capsules formed in step 2, said process being characterized in that the formation of the inorganic precipitate in step 2 is carried out in the presence of an amphiphilic surfactant system present in the emulsion, concentrating a deposit of the precipitated inorganic particles at an interface of the aqueous droplets and of the organosoluble phase and blocking their diffusion within said droplets.

2. The process as claimed in claim 1, wherein the aqueous fluid comprises at least one active material.

3. The process as claimed in claim 1, wherein the amphiphilic surfactant system is composed of a single surfactant introduced prior to carrying out step 2.

4. The process as claimed in claim 1, wherein the amphiphilic surfactant system comprises at least two surfactants, which in situ interact.

5. The process as claimed in claim 4, wherein the amphiphilic surfactant system comprises at least one organosoluble surfactant, present in the organosoluble phase, and one water-soluble compound present in the aqueous fluid.

6. The process as claimed in claim 1, wherein the amphiphilic surfactant system contributes to a stabilization of the emulsion.

7. The process as claimed in claim 1, wherein the surfactant system comprises at least one surfactant having an HLB value of less than 7.

8. The process as claimed in claim 1, wherein the surfactant system comprises at least one surfactant having in its structure at least one branch or group having an HLB value of less than 7.

9. The process as claimed in claim 5, wherein the organosoluble surfactant is a fatty alcohol, a triglyceride, a fatty acid, a sorbitan ester or a fatty amine, optionally in a polyalkoxylated form, a fat-soluble lecithin form, a polyalkylene dipolyhydroxystearate form, a quaternary ammonium salt form, a monoglyceride form, a polyglycerol ester form, a polyglycerol polyricinoleate form or a lactic ester form.

10. The process as claimed in claim 9, wherein the organosoluble surfactant is a sorbitan ester.

11. The process as claimed in claim 5, wherein the water-soluble compound present in the aqueous fluid has a viscosifying effect.

12. The process as claimed in claim 5, wherein the water-soluble compound present in the aqueous fluid is a linear or cyclic $C_3$ to $C_6$ monosaccharide, an oligosaccharide, a polysaccharide, a gelatin, a gelatin fatty derivative, a carbohydrate ether.

13. The process as claimed in claim 5, wherein the water-soluble compound present in the aqueous fluid is fructose, mannose, galactose, talose, gulose, allose, altrose, idose, arabinose, xylose, lyxose, ribose, sucrose, cellobiose, maltose, lactose, starch, cellulose, xanthan gum, carrageenan, guar gum, bean gum, gum arabic, a fatty acid sucroester, a carbohydrate alcohol of sorbitol or mannitol, a methyl, ethyl, carboxymethyl, hydroxyethyl or hydroxypropyl ether of cellulose, glycerol, pentaerythrol, propylene glycol, ethylene glycol or a poly(vinyl alcohol).

14. The process as claimed in claim 5, wherein the water-soluble compound present in the aqueous fluid is a hydrocolloid.

15. The process as claimed in claim 5, characterized in that the water-soluble compound present in the aqueous fluid is an alginate or a polysaccharide of a natural gum.

16. The process as claimed in claim 5, wherein the water-soluble compound present in the aqueous fluid is a cellulose derivative.

17. The process as claimed in claim 1, wherein the aqueous droplets have a size between 0.1 and 10 µm.

18. The process as claimed in claim 17, wherein emulsifying is performed by mechanical means or with ultrasound.

19. The process as claimed in claim 1, wherein the hydrolyzable and polycondensable compound has the general formula (II):

$$M(R)_n(P)_m \tag{II}$$

wherein:

M represents an element chosen in the group consisting of titanium, manganese, iron, cobalt, nickel, silicon, aluminum and zirconium, R is a hydrolyzable group, n is an integer between 1 and 6, P is a nonhydrolyzable substituent, and m is an integer between 0 and 6.

20. The process as claimed in claim 19, characterized in that:

M is silica, aluminum, titanium or zirconium,

R is a $C_1$ to $C_{18}$ alkoxy group or an aryloxy group and n is an integer between 2 and 4, and P is a $C_1$ to $C_{18}$ group.

21. The process as claimed in claim 20, wherein P is a $C_8$ to $C_{12}$ alkyl, aryl, or alkenyl group.

22. The process as claimed in claim 19, wherein the hydrolyzable and polycondensable compound a silicon alkoxide.

23. The process as claimed in claim 22, wherein the silicon alkoxide is the tetramethyl orthosilicate, the tetraethyl orthosilicate or the tetrapropyl orthosilicate.

24. The process as claimed in claim 22, wherein the precipitate is formed in the presence of an agent for hydrolyzing and condensing the silicon alkoxide.

25. The process as claimed in claim 5, wherein the organosoluble surfactant is the sorbitan sesquioleate and the water-soluble compound present in the aqueous fluid is the hydroxyethylcellulose.

26. The process as claimed in claim 1, wherein the aqueous fluid comprises at least one active material for plant protection, cosmetics, pharmaceuticals, and/or chemical make-up.

27. The process as claimed in claim 1, wherein pH in step 2 is between 8 and 11.

28. The process as claimed in claim 1, wherein the capsules have a size of between 1 and about ten micrometers.

* * * * *